United States Patent
Chung et al.

(10) Patent No.: US 10,865,226 B2
(45) Date of Patent: Dec. 15, 2020

(54) PEPTIDE SHOWING MELANOGENESIS PROMOTING ACTIVITY AND USE THEREOF

(71) Applicant: CAREGEN CO., LTD., Anyang-si (KR)

(72) Inventors: Yong Ji Chung, Yongin-si (KR); Eun Mi Kim, Yongin-si (KR); Eung-Ji Lee, Anyang-si (KR)

(73) Assignee: CAREGEN CO., LTD., Anyang-Si (KR)

( * ) Notice: Subject to any disclaimer, the term of this patent is extended or adjusted under 35 U.S.C. 154(b) by 0 days.

(21) Appl. No.: 16/615,899

(22) PCT Filed: Feb. 21, 2018

(86) PCT No.: PCT/KR2018/002109
§ 371 (c)(1),
(2) Date: Nov. 22, 2019

(87) PCT Pub. No.: WO2018/216884
PCT Pub. Date: Nov. 29, 2018

(65) Prior Publication Data
US 2020/0148721 A1  May 14, 2020

(30) Foreign Application Priority Data

May 23, 2017  (KR) .................. 10-2017-0063701

(51) Int. Cl.
| | |
|---|---|
| *A61K 38/08* | (2019.01) |
| *A61K 8/64* | (2006.01) |
| *C07K 7/06* | (2006.01) |
| *C07K 7/08* | (2006.01) |
| *A61Q 19/00* | (2006.01) |
| *A61P 17/00* | (2006.01) |
| *A61K 38/00* | (2006.01) |

(52) U.S. Cl.
CPC .................. *C07K 7/06* (2013.01); *A61K 8/64* (2013.01); *A61Q 19/00* (2013.01); *A61K 38/00* (2013.01); *A61K 2800/10* (2013.01)

(58) Field of Classification Search
CPC .......... A61K 38/08; A61K 8/64; A61Q 19/00; C07K 14/495; C07K 7/06; C07K 7/08; C12N 9/0071; A61P 17/00; C12Y 114/18001
USPC ...... 514/1.1, 21.5, 21.6, 18.6; 530/300, 327, 530/328
See application file for complete search history.

(56) References Cited

U.S. PATENT DOCUMENTS

| | | | |
|---|---|---|---|
| 5,516,891 A | 5/1996 | Siwruk et al. | |
| 7,736,638 B2* | 6/2010 | Savio ................. | C07K 14/5443 424/85.2 |
| 10,093,698 B2 | 10/2018 | Chung et al. | |
| 10,526,373 B2* | 1/2020 | Chung ................... | A61P 17/00 |
| 2012/0190097 A1 | 7/2012 | Castillo et al. | |
| 2019/0119321 A1 | 4/2019 | Chung et al. | |

FOREIGN PATENT DOCUMENTS

| | | |
|---|---|---|
| KR | 10-2012-0084293 A | 7/2012 |
| KR | 10-2015-0130615 A | 11/2015 |
| KR | 10-2017-0097832 A | 8/2017 |

OTHER PUBLICATIONS

Q4LDM3 from uniProtKB, pp. 1-5. Integrated into UniProtKB/TrEMBL on Aug. 2, 2005. (Year: 2005).*
A0A1S3G9L1 from UniProtKB, pp. 1-5. Integrated into UniProtKB/TrEMBL on Apr. 12, 2017. (Year: 2017).*
Fields et al., "Teaching Reading Comprehension to Children with Multiple Impairments, Including Deafblindness," Nevada Dual Sensory Impairment Progject, Winter 2014, 22(2): 1-12. (Year: 2014).*
Shaffer M, "Special disorders of Black Skin," The Washington Post, pp. 1-3. Mar. 27, 1985. (Year: 1985).*
Aberdam et al., "Involvement of microphthalmia in the inhibition of melanocyte lineage differentiation and of melanogenesis by agouti signal protein," J Biol Chem. 273(31):19560-5 (1998) (7 pages).
International Search Report, dated Jun. 1, 2018, for PCT International Application No. PCT/KR2018/002109, Chung et al., "Peptide Showing Melanogenesis Promoting Activity and Use Thereof," filed Feb. 21, 2018 (6 pages).
Merrifield, "Solid Phase Peptide Synthesis. I. The Synthesis of a Tetrapeptide," J Am Chem Soc. 85:2149-54 (1963) (6 pages).
Sarkar et al., "Human placental protein/peptides stimulate melanin synthesis by enhancing tyrosinase gene expression," Mol Cell Biochem. 285(1-2):133-42 (2006).

* cited by examiner

*Primary Examiner* — Julie Ha
(74) *Attorney, Agent, or Firm* — Clark & Elbing LLP; Susan M. Michaud

(57) ABSTRACT

Peptides exhibiting melanogenesis promoting activity are described. The peptides increase the activity and expression of tyrosinase and the expression of factors involved in melanogenesis, thereby exhibiting an outstanding effect on melanogenesis. The peptides can be used for the prevention, alleviation, and treatment of hypomelanosis. The outstanding activity and stability stated above allow the peptides to be very favorably applied to medicines, quasi-medicines, and cosmetics.

20 Claims, 15 Drawing Sheets

Specification includes a Sequence Listing.

PEPTIDE SHOWING MELANOGENESIS PROMOTING ACTIVITY AND USE THEREOF

SEQUENCE LISTING

The instant application contains a Sequence Listing which has been submitted electronically in ASCII format and is hereby incorporated by reference in its entirety. Said ASCII copy, created on Nov. 20, 2019 is named 51401_015001_Sequence_Listing_112019_ST25 and is 2,071 bytes in size.

TECHNICAL FIELD

The present invention relates to a peptide exhibiting melanogenesis promoting activity; a pharmaceutical composition containing the peptide as an active ingredient, for prevention and/or treatment of hypomelanosis; a cosmetic composition containing the peptide as an active ingredient, for prevention and/or alleviation of hypomelanosis; and a use of the peptide for prevention, alleviation, and/or treatment of hypomelanosis.

BACKGROUND ART

In skin cells, melanin is produced in melanosomes of melanocytes in the epidermal stratum basale as a defense mechanism against the stimuli of ultraviolet (UV) light, environmental pollution, and other external factors. Melanin is an important factor in determining the color of the skin, eyes, and hair of animals. Hypomelanosis is also known as a risk factor for skin cancer. East Asians are sensitive to the overproduction of melanin, and thus much research has been conducted on whitening in which melanogenesis is inhibited. In recent years, the demand for treatment of vitiligo, which is caused by melanogenesis inhibition, is also increasing, and thus research thereon is in progress.

Vitiligo is an acquired depigmentation disease in which milky spots of various sizes and shapes appear due to apoptosis or necrosis of melanocytes. Vitiligo is a relatively common disease that occurs in about 1% of the world's population, and there is no difference in the disease according to race or region. Regarding the age of occurrence, vitiligo occurs most frequently at ages of 10 to 30 years, with 95% of cases occurring before the age of 40, and 30% of patients having a family history.

The cause of vitiligo has not yet been accurately identified, but there are various theories, such as the autoimmune theory, the neural theory, and melanocyte self-destruction theory. The autoimmune theory is that the destruction or dysfunction of melanocytes is caused by the expression of auto-antibodies to melanocyte-based antigens, or melanocytes are destroyed by lymphokines secreted by cytotoxic lymphocytes or activated lymphocytes. The neural theory is that hydrogen peroxide associated with stress is generated due to abnormal catecholamine biosynthesis and increased monoamine oxidase, resulting in the destruction of melanocytes, and vitiligo may occur along the ganglion or vitiligo may occur after nerve damage or stress. The melanocyte self-destruction theory is that intermediate metabolites or phenol complexes as final metabolites of the melanogenic process accumulate in melanocytes, resulting in cell destruction. In addition, various factors, such as inherent cellular defects, genetic factors, apoptosis, calcium metabolism disorders, have been suggested.

Melanin is synthesized in melanocytes, and plays an important role in skin protection against UV irradiation or the absorption of toxic substances and chemical substances. Therefore, in people whose melanin synthesis does not occur normally, there is a problem with appearance in that part of the skin, rather than all of the skin, becomes white, causing blotches, and there is a severe problem of being sensitive to external stimuli.

Tyrosinase, tyrosinase related protein-1 (TRP-1), and tyrosinase related protein-2 (TRP-2), which are important enzymes in melanin synthesis, act as catalysts for oxidative reactions (Pigment Cell Res. 14 (6): 43744).

Here, tyrosinase acts to oxidize tyrosine into L-3,4-dihydroxyphenylalanine (DOPA) and DOPA into DOPA quinone, and TRP-1 is a dihydroxyindole carboxylic acid oxidase that is involved in the conversion of 5,6-dihydroxyindole-2-carboxylic acid (DHICA) into indol-5,6-quinone-2-carboxylic acid. TRP-1 also serves to stabilize tyrosinase and regulate activity thereof. TRP-2, which is a DOPA chrome tautomerase, converts DOPA chrome into DHICA to form eumelanin and pheomelanin, which constitute melanocytes, and the ratio thereof determines the colors of skin, hair, and eyes.

Melanin synthesis is activated by UV irradiation and α-melanocyte stimulating hormone (MSH). Here, α-MSH, which is a peptide hormone, is known to be produced by UV light and made from several cells including those of the pituitary gland and skin.

Here, α-MSH acts on melanocortin receptors (MCR) of melanocytes by paracrine signaling to regulate the activity of the transcription factor, microphthalmia-associated transcription factor (MITF), thereby regulating the activity of tyrosinase, DHICA oxidase (TRP-1), and DOPAchrome tautomerase (TRP-2), which play important roles in melanin synthesis (THE JOURNAL OF BIOLOGICAL CHEMISTRY Vol. 273, No. 31, Issue of July 31, pp. 195609565, 1998).

It has been reported that the stimulation of melanocytes by UV or α-MSH leads to the activation of tyrosinase by p38 or protein kinase A (PKA), respectively. In these two pathways, especially, the α-MSH→cAMP→PKA pathway plays an important role in melanin synthesis. The increase in cAMP stimulates the phosphorylation of cAMP-responsive element binding protein (CREB), increasing the expression of the transcription factor MITF, which enhances the activity of tyrosinase and increases the mRNA expression of tyrosinase (Nucleic Acids Res. 30 (14): 3096106, Pigment Cell Melanoma Res 21 (6): 66576).

Many East Asian people including Koreans want to have light skin color, and thus much research has been conducted on whitening components which inhibit melanogenesis. However, melanin is synthesized in melanocytes in the skin, and plays an important role in skin protection from UV irradiation or the absorption of toxic substances and chemical substances. Since the absence of normal synthesis of melanin makes the skin sensitive to external stimuli and results in an abnormal external appearance, there is a need to treat melanin synthesis so that melanin synthesis can be normalized, and studies on this have also been conducted. However, so far, the development of technology for promoting melanin synthesis has not been carried out sufficiently.

DESCRIPTION OF EMBODIMENTS

Technical Problem

The present inventors endeavored to develop peptides capable of promoting melanogenesis, and as a result, the present inventors confirmed that a peptide including a sequence selected from the group consisting of the acid sequences of SEQ ID NO: 1, SEQ ID NO: 2, and SEQ ID NO: 3 has excellent melanogenesis promoting activity and established that these peptides may be useful in the prevention and treatment of hypomelanosis, and thus the present inventors completed the present invention.

Therefore, provided is a peptide showing melanogenesis promoting activity, the peptide including the amino acid sequence of SEQ ID NO: 1, SEQ ID NO: 2, or SEQ ID NO: 3.

Provided is a pharmaceutical composition for preventing and/or treating hypomelanosis, the pharmaceutical composition containing, as an active ingredient, at least one peptide selected from the group consisting of peptides each including a sequence selected from the group consisting of the amino acid sequence of SEQ ID NO: 1, the amino acid sequence of SEQ ID NO: 2, and the amino acid sequence of SEQ ID NO: 3.

Provided is a cosmetic composition for prevention and/or alleviation of hypomelanosis, the cosmetic composition containing, as an active ingredient, at least one peptide selected from the group consisting of peptides each including a sequence selected from the group consisting of the amino acid sequence of SEQ ID NO: 1, the amino acid sequence of SEQ ID NO: 2, and the amino acid sequence of SEQ ID NO: 3.

Solution to Problem

According to an aspect of the present invention, the present inventors have tried to develop a peptide capable of promoting melanogenesis, and as a result, it was confirmed that a peptide containing the amino acid sequence of SEQ ID NO: 1, SEQ ID NO: 2, or SEQ ID NO: 3 has excellent melanogenesis promoting activity and established that the peptide may be favorably used in the prevention and treatment of hypomelanosis.

Thus, the present invention is related to a peptide showing melanogenesis promoting activity; a pharmaceutical composition containing the peptide as an active ingredient for prevention and/or treatment of hypomelanosis; a cosmetic composition containing the peptide as an active ingredient for prevention and/or alleviation of hypomelanosis; and a use of the peptide for prevention, alleviation, and/or treatment of hypomelanosis.

Hereinafter, the present invention will be described in further detail.

According to an embodiment of the present invention, a peptide includes the amino acid sequence of SEQ ID NO: 1, SEQ ID NO: 2, or SEQ ID NO: 3.

The peptide according to an embodiment may include the amino acid sequence of SEQ ID NO: 1, SEQ ID NO: 2, or SEQ ID NO: 3, and, for example, may consist of the amino acid sequence of SEQ ID NO: 1, SEQ ID NO: 2, or SEQ ID NO: 3.

The peptide may show melanogenesis promoting activity.

The peptide of the present invention is obtained by screening peptides, which have excellent melanogenesis promotion effects, from peptide libraries possessed by the present inventors, through experiments about gene and protein expression changes, and a total of three types of peptides are provided as a peptide of the present invention.

As used herein, the term "peptide" refers to a linear molecule formed of amino acid residues link to each other via peptide bonds. The peptide of the present invention may be prepared by known chemical synthesis methods, especially, solid-phase synthesis techniques (Merrifield, *J. Amer. Chem. Soc.* 85:2149-54 (1963); Stewart, et al., *Solid Phase Peptide Synthesis*, 2nd. ed., Pierce Chem. Co.: Rockford, 111 (1984)) or liquid-phase synthesis techniques (U.S. Pat. No. 5,516,891).

The peptide of the present invention may have a modification induced at the N-terminal and/or C-terminal thereof in order to select a part of an amino acid sequence and increase the activity thereof.

The N-terminal and/or C-terminal modification of the peptide improves the stability of the peptide, and this modification allows the peptide of the present invention to have an increased half-life at the time of in vivo administration, thereby having a high half-life.

Also, the C-terminal and/or N-terminal modification may protect the peptide of the present invention from in vivo protein cleavage enzymes or may increase binding force to a receptor.

For example, the C-terminal modification may be a modification of the C-terminal of the peptide into a hydroxyl group (—OH), an amino group (—$NH_2$), or an azide group (—$NHNH_2$), but embodiments are not limited thereto.

The N-terminal modification may be an attachment of at least one protecting group selected from the group consisting of an acetyl group, a fluorenyl methoxy carbonyl group, a formyl group, a palmitoyl group, a myristyl group, a stearyl group, and polyethylene glycol (PEG) to the N-terminal of the peptide, but embodiments are not limited thereto.

As used herein, the term "stability" refers to storage stability (e.g., room-temperature stability) as well as in vivo stability.

According to an aspect of the present invention, the peptide of the present invention increases the melanogenesis in melanocytes, increases the activity and expression of tyrosinase, which is an enzyme for regulating melanin synthesis, increases the expression of MITF and TRP1 and increases the phosphorylation of CREB, these being factors involved in melanogenesis.

These results indicate that the peptide of the present invention has an effect of relieving vitiligo by increasing melanogenesis. Therefore, the peptide of the present invention can be used for the prevention, alleviation, and/or treatment of hypomelanosis.

In the present invention, the hypomelanosis may be vitiligo, albinism, nevus depigmentosus, pityriasis alba, pityriasis versicolor, post-inflammatory depigmentation, morphea, piebaldism, idiopathic guttate hypomelanosis, or leucoderma punctatum.

According to another aspect of the present invention, a pharmaceutical composition for prevention or treatment of hypomelanosis contains, as an active ingredient, at least one peptide selected from the group consisting of a peptide consisting of the amino acid sequence of SEQ ID NO: 1, a peptide consisting of the amino acid sequence of SEQ ID NO: 2, and a peptide consisting of the amino acid sequence of SEQ ID NO: 3.

Since the pharmaceutical composition of the present invention contains the foregoing peptide of the present invention as an active ingredient, the descriptions of overlapping contents therebetween will be omitted to avoid excessive complexity of the present specification.

The pharmaceutical composition of the present invention may contain a pharmaceutically effective amount of the foregoing peptide of the present invention.

As used herein, the term "pharmaceutically effective amount" refers to an amount sufficient to attain the efficacy or activity of the foregoing peptide.

The pharmaceutical composition may further include a pharmaceutically acceptable carrier, but embodiments are not limited thereto.

Examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and/or mineral oil, but embodiments are not limited thereto.

The pharmaceutical composition of the present invention may further include a lubricant, a wetting agent, a sweetening agent, a flavoring agent, an emulsifier, a suspending agent, and a preservative, in addition to the above ingredients.

The pharmaceutical composition of the present invention may be in the form appropriate for the desired administration method.

In terms of the pharmaceutical composition of the present invention, the expression "administration" denotes introducing a predetermined material to a patient by using an appropriate method.

The pharmaceutical composition of the present invention may be administered through a general rout as long as the drug may reach the target tissue. For example, the drug may be administered by intraperitoneal administration, intravenous administration, intramuscular administration, subcutaneous administration, intradermal administration, oral administration, topical administration, intranasal administration, pulmonary administration, or rectal administration. In some embodiments, the drug may be administered, preferably, by parenteral administration or, more preferably, by topical skin administration.

Also, the pharmaceutical composition of the present invention may be administered by using a device that may transfer the active ingredient to a target cell.

The appropriate dose of the pharmaceutical composition of the present invention varies depending on factors, such as a formulating method, a manner of administration, patient's age, body weight, gender, morbidity, food, a time of administration, a route of administration, an excretion rate, and response sensitivity. The ordinarily skilled practitioners may easily determine and prescribe the dose that is effective for the desired treatment or prevention. According to a preferable embodiment of the present invention, the daily dose of the pharmaceutical composition of the present invention is 0.001 to 1000 mg/kg.

The pharmaceutical composition of the present invention is formulated using a pharmaceutically acceptable carrier and/or excipient according to a method that is easily conducted by a person having ordinary skills in the art to which the present invention pertains, and the pharmaceutical composition of the present invention may be prepared into a unit dosage form or may be inserted into a multi-dose container.

Here, the dosage form may be a solution in an oily or aqueous medium, a suspension, an emulsion, an extract, a powder, granules, a tablet, a capsule, or a gel (e.g., a hydrogel), and may further contain a dispersing agent or a stabilizer.

According to another aspect of the present invention, a cosmetic composition for preventing or alleviating hypomelanosis contains, as an active ingredient, at least one peptide selected from the group consisting of a peptide consisting of the amino acid sequence of SEQ ID NO: 1, a peptide consisting of the amino acid sequence of SEQ ID NO: 2, and a peptide consisting of the amino acid sequence of SEQ ID NO: 3.

The cosmetic composition of the present invention may include a cosmetically effective amount of the foregoing peptide of the present invention.

As used herein, the term "cosmetically effective amount" refers to an amount sufficient to attain the efficacy of the foregoing composition of the present invention.

In addition, the cosmetic composition may further include a cosmetically acceptable carrier, but embodiments are not limited thereto.

The cosmetic composition of the present invention may be formulated into any form that is commonly prepared into, and examples of the form may include a solution, a suspension, an emulsion, a paste, a gel, a cream, a lotion, a powder, a soap, a surfactant-containing cleanser, an oil, a powder foundation, an emulsion foundation, a wax foundation, and/or a spray, but embodiments are not limited thereto. More specifically, the cosmetic composition of the present invention may be prepared in the form of emollient lotion, nourishing lotion, nourishing cream, massage cream, essence, eye cream, cleansing cream, cleansing foam, cleansing water, pack, spray, and/or powder.

In cases where the form of the cosmetic composition is a paste, cream, or gel, useful examples of the carrier ingredient may include an animal oil, a plant oil, wax, paraffin, starch, tragacanth, a cellulose derivative, polyethylene glycol, silicone, bentonite, silica, talc, and/or zinc oxide, but embodiments are not limited thereto.

When the form of the cosmetic composition is a powder or spray, lactose, talc, silica, aluminum hydroxide, calcium silicate, or a polyamide powder may be used as a carrier ingredient, but embodiments are not limited thereto. Especially, when the form of the cosmetic composition of the present invention is a spray, the spray may further include a propellant, such as chlorofluorohydrocarbon, propane/butane, and/or dimethyl ether, but embodiments are not limited thereto.

When the form of the cosmetic composition is a solution or emulsion, a solvent, solubilizer, or emulsifier may be used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic esters, polyethylene glycol, and/or fatty acid esters of sorbitan.

When the form of the cosmetic composition is a suspension, examples of the carrier ingredient may include a liquid diluent (such as water, ethanol, and/or propylene glycol), a suspending agent (such as ethoxylated isostearyl alcohol, polyoxyethylene sorbitol ester, and/or polyoxyethylene sorbitan ester), microcrystalline cellulose, aluminum metahydroxide, bentonite, agar, and/or tragacanth, but embodiments are not limited thereto.

When the form of the cosmetic composition is a surfactant-containing cleanser, examples of the carrier ingredient may be aliphatic alcohol sulfate, aliphatic alcohol ether sulfate, sulfosuccinate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives, and/or ethoxylated glycerol fatty acid ester, but embodiments are not limited thereto.

In addition to the peptide and carrier ingredients, components contained in the cosmetic composition of the present invention as the active ingredients may include ingredients ordinarily used in cosmetic compositions, and examples thereof may include ordinary supplements, such as an antioxidant, a stabilizer, a solubilizer, vitamins, a pigment, and/or a flavoring agent, but embodiments are not limited thereto.

Advantageous Effects of Disclosure

The present invention is directed to a peptide showing melanogenesis promoting activity; a pharmaceutical composition including the peptide as an active ingredient for prevention and/or treatment of hypomelanosis; a cosmetic composition including the peptide as an active ingredient for prevention and/or alleviation of hypomelanosis; and a use of the peptide for prevention, alleviation, and/or treatment of hypomelanosis. The peptide of the present invention increases the activity and expression of tyrosinase and increases the expression of factors involved in melanogenesis, thereby exhibiting excellent effects in melanogenesis, and may be very favorably applied to medicines, quasi-medicines, and cosmetics through excellent activity and safety thereof.

BEST MODE

Figure 1:
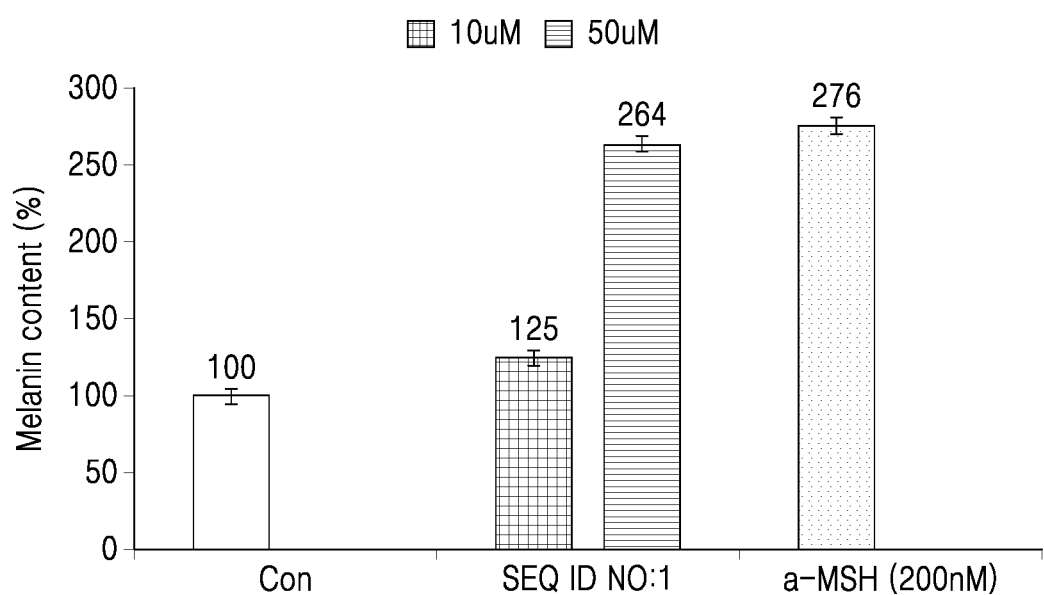
FIG. 1 is a graph that confirms a melanogenesis increasing effect of a peptide consisting of the amino acid sequence of SEQ ID NO: 1 according to an embodiment of the present invention.

Provided is a peptide consisting of the amino acid sequence of SEQ ID NO: 1, 2, or 3.

Mode of Disclosure

Hereinafter, the present invention will be described in detail with reference to examples. However, these examples are only for illustrative purposes, and the scope of the present invention is not limited by these examples.

Synthetic Example 1: Peptide Synthesis 70 g of chlorotrityl chloride resin (CTC resin, Nova Biochem Cat No. 01-64-0021) was added into a reaction container, and 490 ml of methylene chloride (MC) was added followed by stirring for 3 minutes. After the solution was removed, 490 ml of dimethyl formamide (DMF) was added, followed by stirring for 3 minutes, and then the solvent was again removed. 700 ml of a dichloromethane solution was added to a reaction container, and 200 mmole of Fmoc-Leu-OH (Bachem, Swiss) and 400 mmole of diisopropyl ethylamine (DIEA) were added. Thereafter, the mixture was well dissolved with stirring, and then the reaction was conducted with stirring for 1 hour. After the reaction, washing was conducted, and then methanol and DIEA (2:1) were dissolved in dichloromethane (DCM), followed by reaction for 10 minutes, and then the resultant was washed with excess DCM/DMF (1:1). After the solution was removed, 490 ml of dimethyl formamide (DMF) was added, followed by stirring for 3 minutes, and then the solvent was again removed. 700 ml of a deprotection solution (20% piperidine/DMF) was added to a reaction container, followed by stirring at room temperature for 10 minutes, and then the solution was removed. An equal amount of a deprotection solution was added, and then the reaction was again maintained for 10 minutes, and thereafter, the solution was removed, followed by washing twice with DMF, once with MC, and once with DMF, for 3 minutes each, thereby preparing Leu-CTC resin.

700 ml of a DMF solution was added to a new reaction container, and 200 mmol Fmoc-Ser(tBu)-OH (Bachem, Swiss), 200 mmol HoBt, and 200 mmole of HBTu were added, and the mixture was well dissolved with stirring. 400 mmole DIEA was added to the reaction container in two divided portions, and then stirring was conducted for at least 5 minutes until all solids were dissolved. The dissolved amino acid mixed solution was added to the reaction container containing the deprotected resin, and the reaction was conducted with stirring at room temperature for 1 hour. After the reaction solution was removed, the stirring was conducted using a DMF solution three times for 5 minutes each, followed by removal. A small amount of the reaction resin was taken to check the extent of reaction using the Kaiser test (Ninhydrin test). The deprotection reaction was twice conducted using a deprotection solution in the same manner as described above, thereby preparing Ser(tBu)-Leu-CTC resin. After sufficient washing with DMF and MC, the Kaiser test was again conducted, and then the following amino acid attachment test was conducted in the same manner as described above. A chain reaction was conducted in the order of Fmoc-Trp-OH, Fmoc-Ile-OH, Fmoc-Tyr (tBu)-OH, Fmoc-Pro-OH, Fmoc-Cys(Trt)-OH, Fmoc-Pro-OH, Fmoc-Gly-OH, Fmoc-Leu-OH, Fmoc-Cys(Trt)-OH, Fmoc-Phe-OH on the basis of the selected amino acid sequence. The Fmoc-protecting group was removed by reaction twice with the deprotection solution for 10 minutes for each and then favorable washing. The peptidyl resin was washed with DMF, MC, and methanol three times for each, dried under the flow of nitrogen gas, and completely dried by decompression under vacuum in $P_2O_5$. Thereafter, 1,900 ml of a leaving solution [81.5% of trifluoroacetic acid (TFA), 5.0% of distilled water, 5.0% of thioanisole, 5.0% of phenol, 2.5% of ethanedithiol (EDT), and 1.0% of triisopropylsilane (TIS)] was added, and the reaction was maintained for 2 hours while stirring the mixture at room temperature. The resin was obtained through filtration, washed with a small amount of TFA solution, and then mixed with the stock solution. Cold ether was added to 2,090 ml of the resultant with the stock solution to induce precipitation, and the precipitates were collected by centrifugation, followed by washing twice with cold ether. The stock solution was removed, followed by sufficient drying under nitrogen atmosphere, and thus 129.8 g of a peptide consisting of the amino acid sequence of SEQ ID NO: 1 (yield: 92.8%) was synthesized, before purification. The molecular weight was determined as 1398.6 (theoretical value: 1398.6) by using a molecular weight analysis system.

In addition, the peptide composed of the amino acid sequence of SEQ ID NO: 2 or SEQ ID NO: 3 was synthesized in the same manner as described above.

TABLE 1

| SEQ ID NO: | Sequence listing (5'→3') | Analysis value (Mass spectrometer) | |
|---|---|---|---|
| | | Analytical value | Theoretical value |
| 1 | FCLGPCPYIWSL | 1398.6 | 1398.6 |
| 2 | KVTAMRCFLL | 1181.5 | 1181.5 |
| 3 | RVTAMRCFLL | 1209.5 | 1209.5 |

Example 1: Melanogenesis Assay

After seeding melanocytes (B16F10 cell line) in 6-well plates at the density of $5 \times 10^4$ cells/well, the melanocytes were cultured in an incubator at a temperature of 37° C. for 24 hours, and the medium of each plate was removed and replaced with 2% serum-containing media, followed by treatment with the present peptide at different concentrations and then incubation of 72 hours.

Figure 6:
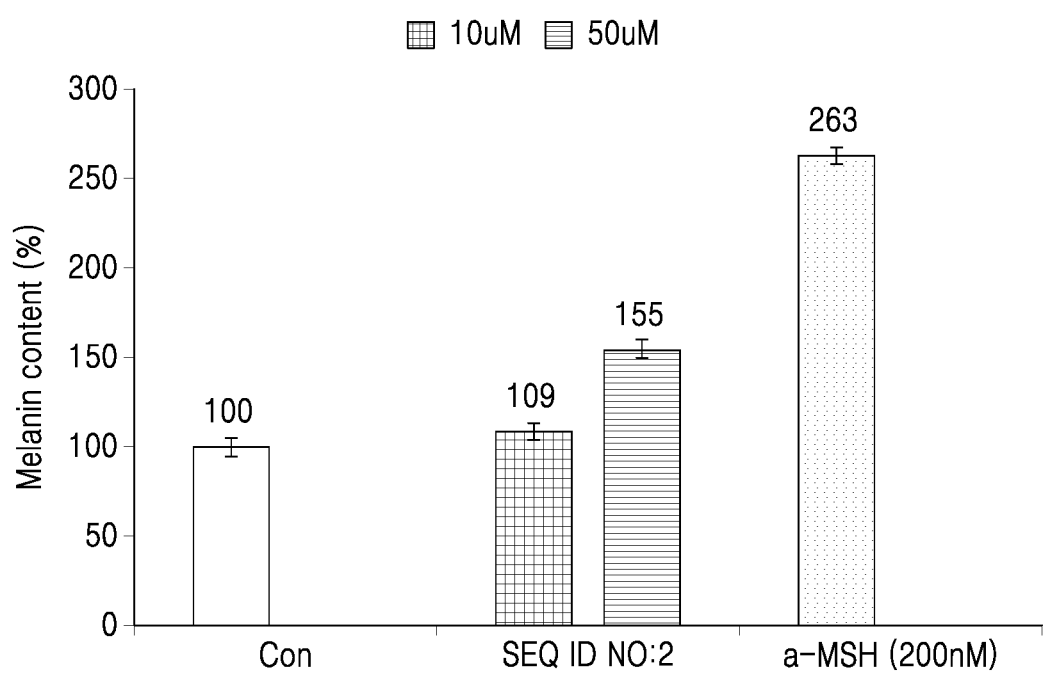
FIG. 6 is a graph that confirms a melanogenesis increasing effect of a peptide consisting of the amino acid sequence of SEQ ID NO: 2 according to an embodiment of the present invention.
Figure 11:
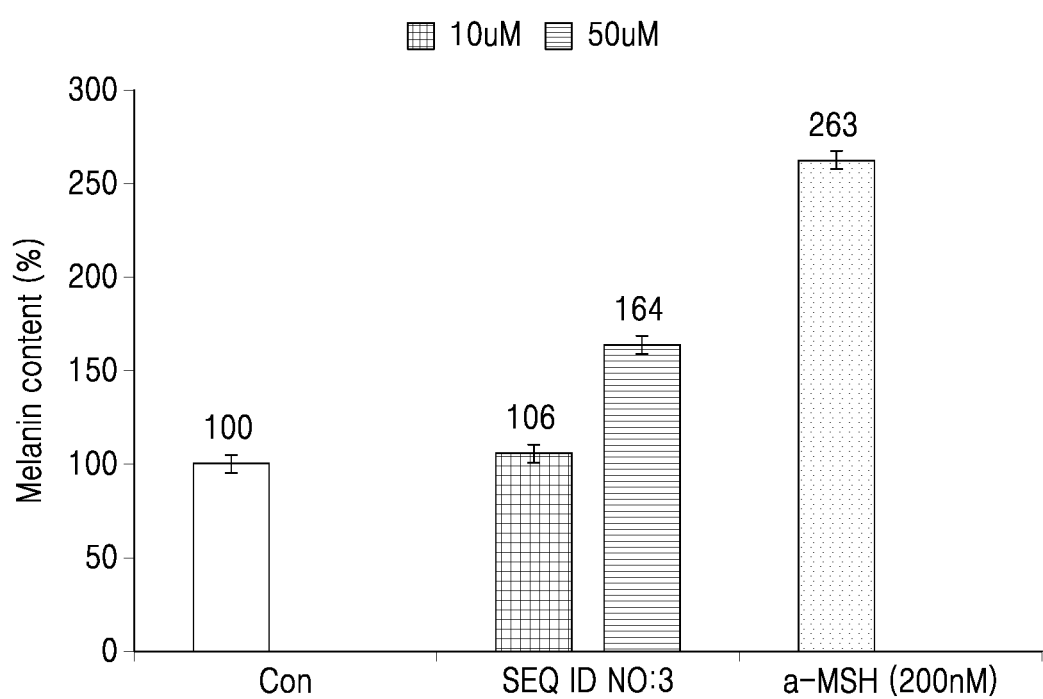
FIG. 11 is a graph that confirms a melanogenesis increasing effect of a peptide consisting of the amino acid sequence of SEQ ID NO: 3 according to an embodiment of the present invention.

Then, the culture medium was removed, and the cells were taken off and then transferred into 1.5-ml tubes, followed by centrifugation at 13,000 rpm for 3 minutes to remove the supernatant. Next, cell pellets were collected to observe melanin. 150 μl of 1 N NaOH was added to the cell pellets to lyse intracellular melanin at a temperature of 60° C. for 30 minutes. Thereafter, 100 μl of the supernatant obtained from the lysis was added into each well of 96-well plates, and the absorbance was measured at 450 nm, and the results are shown in FIGS. 1, 6, and 11 and Tables 2 and 4.

TABLE 2

| | Control group | SEQ ID NO: 1 (10 μM) | SEQ ID NO: 1 (50 μM) | a-MSH (200 nM) |
|---|---|---|---|---|
| Melanin content (%) | 100 | 125 | 264 | 276 |

TABLE 3

| | Control group | SEQ ID NO: 2 (10 μM) | SEQ ID NO: 2 (50 μM) | a-MSH (200 nM) |
|---|---|---|---|---|
| Melanin content (%) | 100 | 109 | 155 | 263 |

TABLE 4

| | Control group | SEQ ID NO: 3 (10 μM) | SEQ ID NO: 3 (50 μM) | a-MSH (200 nM) |
|---|---|---|---|---|
| Melanin content (%) | 100 | 106 | 164 | 263 |

As it may be confirmed in FIGS. 1, 6, and 11 and Tables 2 and 4, melanogenesis was increased when mouse melanin cell line B16F10 was treated with the peptide consisting of the amino acid sequence of SEQ ID NO: 1, 2, or 3.

Example 2: Tyrosinase Activity Assay

Melanoma cell line (B16F10) cells were cultured in 6-well culture plates for 24 hours, and treated with the peptide with different concentrations, followed by culture for 72 hours. The 6-well culture plates were loaded on ice and washed with cool PBS, and then 300 μl of 0.1 M sodium phosphate buffer (pH 6.8, lysis buffer) containing 1% Triton X-100 was added. The cells were collected in 1.5-ml tubes, and then cell membranes were disrupted by repeating five times rapid-freezing at −270° C. and thawing. After centrifugation at 15,000 rpm for 10 minutes, the supernatant was collected in other 1.5-mL tubes, and the protein of the samples was quantified. The samples were diluted to have the same protein concentration and then dispensed in every three wells in 96-well culture plates, and then 20 μl of 10 mM L-DOPA was added, followed by incubation at 37° C. for 1 hour The blank and positive control were as shown in Table 5.

TABLE 5

|  | Sample | Blank | Positive control |
|---|---|---|---|
| Sample | 90 μl | — | — |
| Buffer | — | 90 μl | 80 μl |
| Mushroom tyrosinase (0.1 mg/ml) | — | — | 10 μl |

Figure 2:
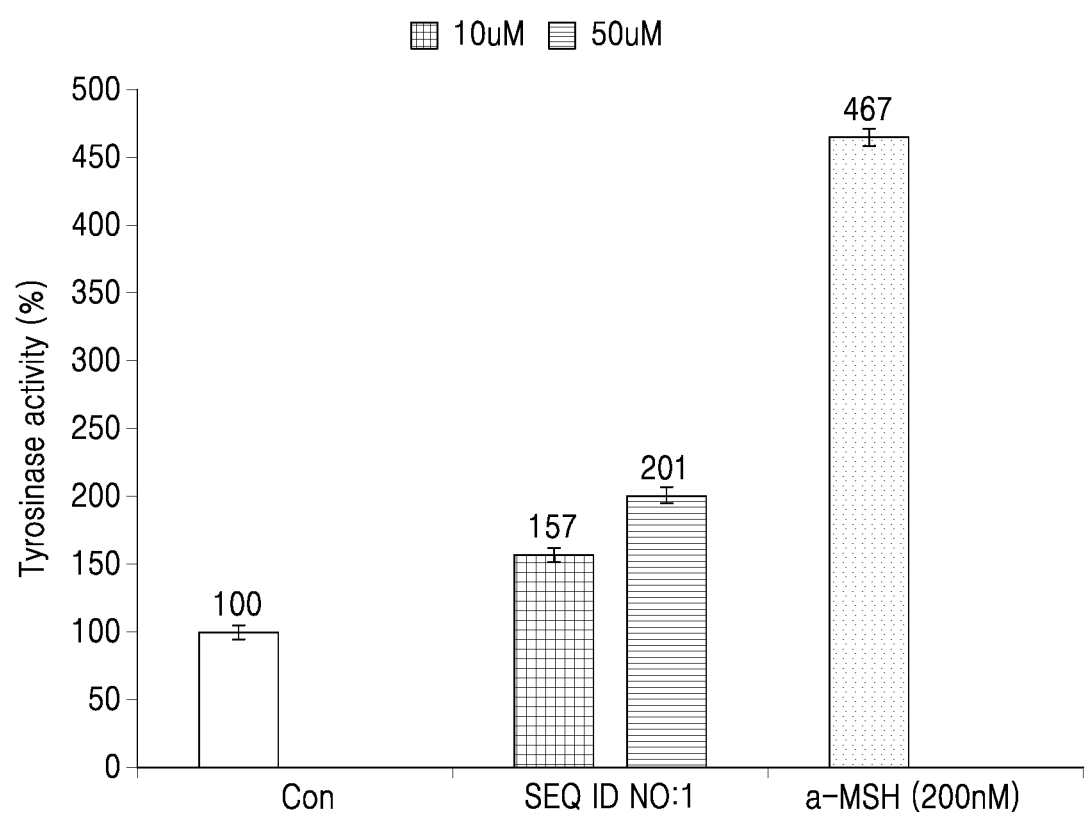
FIG. 2 is a graph that confirms a tyrosinase increasing effect of a peptide consisting of the amino acid sequence of SEQ ID NO: 1 according to an embodiment of the present invention.
Figure 7:
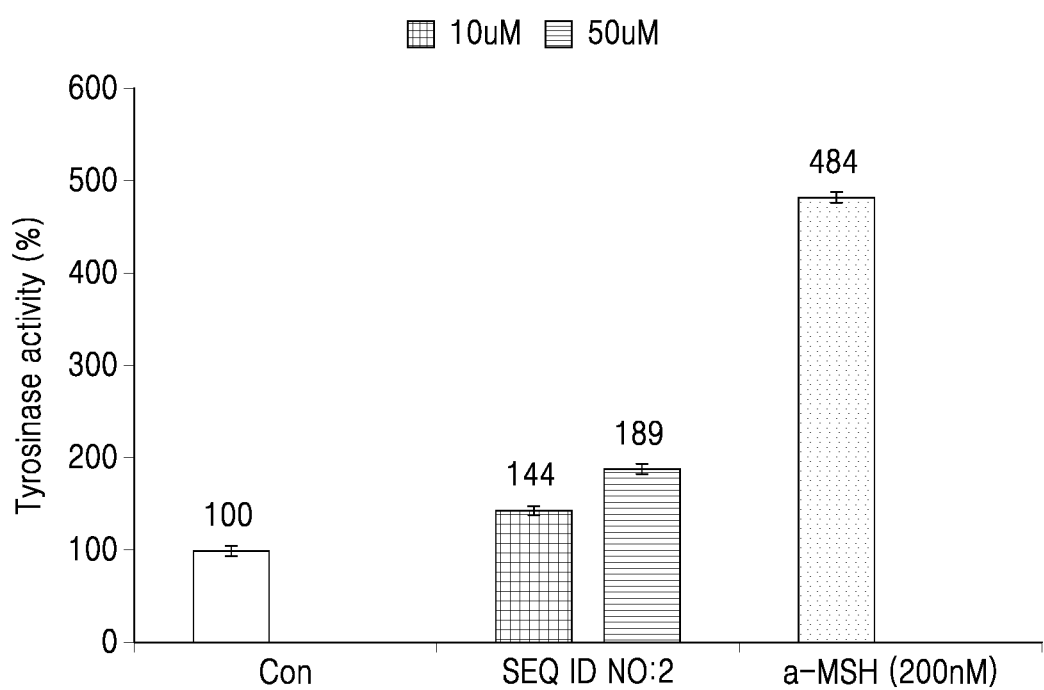
FIG. 7 is a graph that confirms a tyrosinase activity increasing effect of a peptide consisting of the amino acid sequence of SEQ ID NO: 2 according to an embodiment of the present invention.
Figure 12:
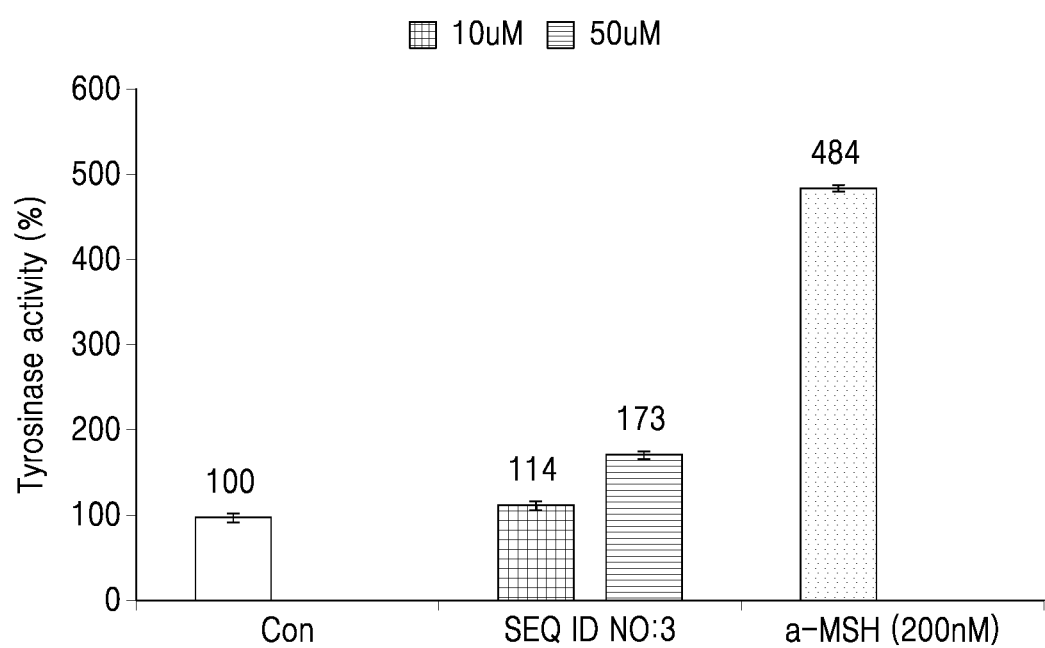
FIG. 12 is a graph that confirms a tyrosinase activity increasing effect of a peptide consisting of the amino acid sequence of SEQ ID NO: 3 according to an embodiment of the present invention.

Then, the absorbance was measured at 475 nm, and the results are shown in FIGS. 2, 7, and 12, and Tables 6 to 8.

TABLE 6

|  | Control group | SEQ ID NO: 1 (10 μM) | SEQ ID NO: 1 (50 μM) | a-MSH (200 nM) |
|---|---|---|---|---|
| Tyrosinase activity (%) | 100 | 157 | 201 | 467 |

TABLE 7

|  | Control group | SEQ ID NO: 2 (10 μM) | SEQ ID NO: 2 (50 μM) | a-MSH (200 nM) |
|---|---|---|---|---|
| Tyrosinase activity (%) | 100 | 144 | 189 | 484 |

TABLE 8

|  | Control group | SEQ ID NO: 3 (10 μM) | SEQ ID NO: 3 (50 μM) | a-MSH (200 nM) |
|---|---|---|---|---|
| Tyrosinase activity (%) | 100 | 114 | 173 | 484 |

As it may be confirmed in FIGS. 2, 7, and 12 and Tables 6 to 8, tyrosinase activity was increased when mouse melanin cell line B16F10 was treated with the peptide composed of the amino acid sequence of SEQ ID NO: 1, 2, or 3.

Example 3: RT-PCR of Melanogenesis-Related Genes

Figure 3:
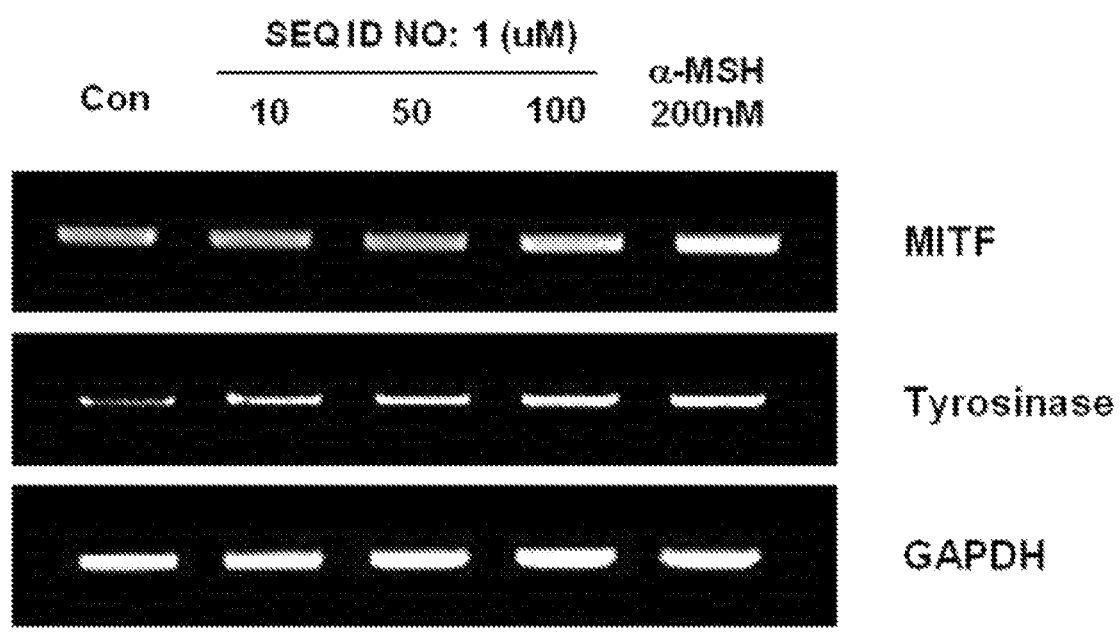
FIG. 3 shows a melanogenesis-related gene expression increasing effect of a peptide consisting of the amino acid sequence of SEQ ID NO: 1 according to an embodiment of the present invention.
Figure 8:
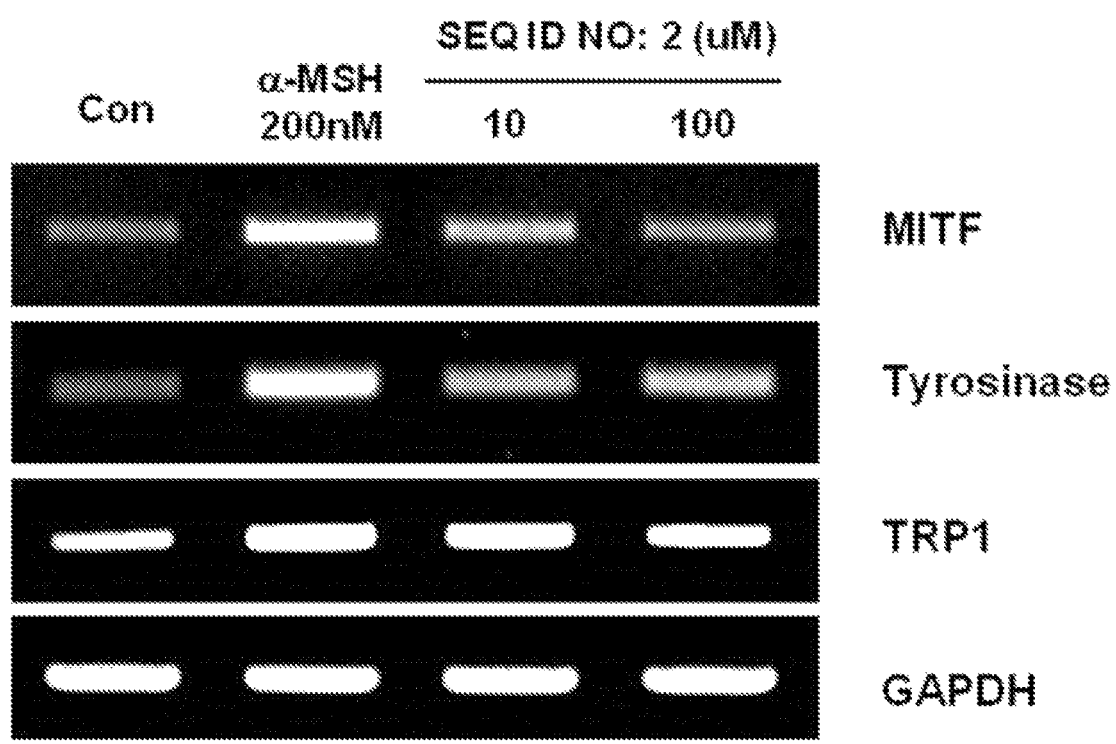
FIG. 8 is a graph that confirms a melanogenesis-related gene expression increasing effect of a peptide consisting of the amino acid sequence of SEQ ID NO: 2 according to an embodiment of the present invention.
Figure 13:
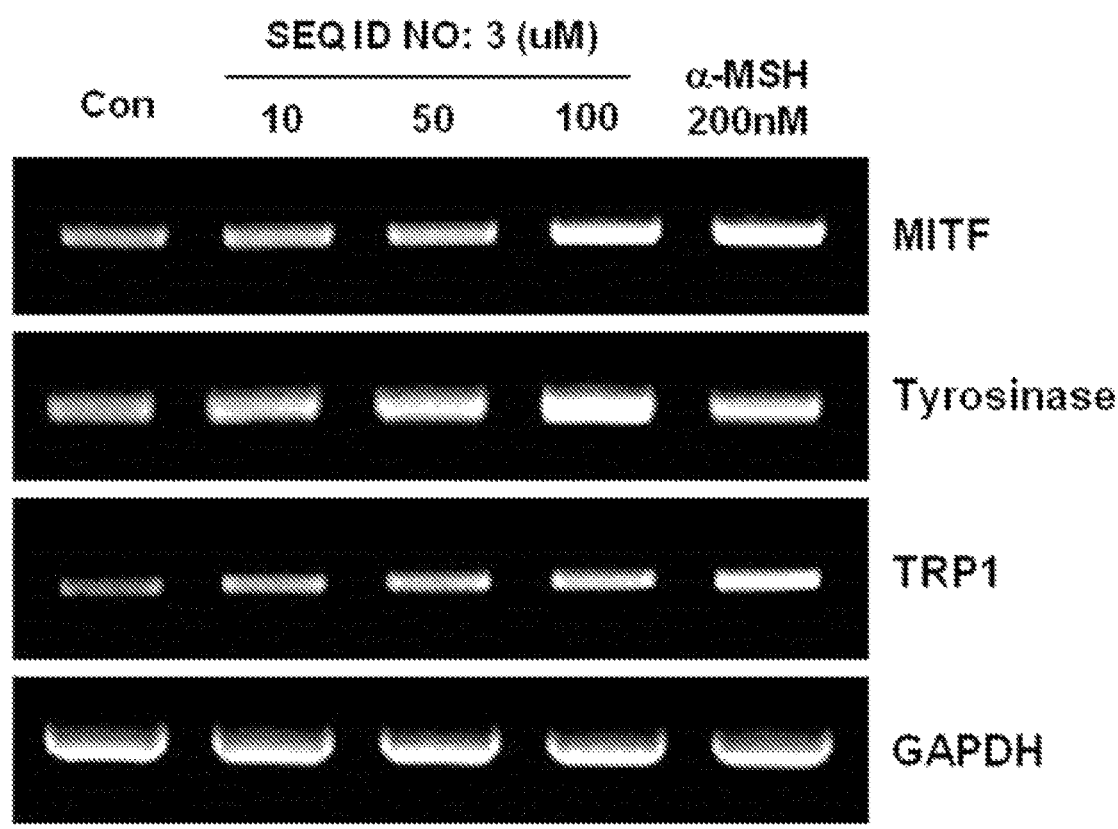
FIG. 13 is a graph that confirms a melanogenesis-related gene expression increasing effect of a peptide consisting of the amino acid sequence of SEQ ID NO: 3 according to an embodiment of the present invention.

Melanocytes (B16F10 cell line) were seeded on 6-well culture plates at the density of 5×10$^4$ cells/well and incubated in an incubator for 24 hours. Then, the medium was replaced with 00, and the cells were treated with the peptides of the present invention with different concentrations and cultured for 72 hours. Next, after RNA extraction of cells and quantification, cDNA was synthesized by using the cDNA synthesis kit (Intron, Korea). Thereafter, as shown in Table 3, PCR was performed using specific primers for MITF, tyrosinase, and TRP1, which are factors involved in melanogenesis. Then, degrees of mRNA expression of the growth factors under each sample treatment conditions were compared by running the resultants on a 5% agarose gel, and the results are shown in FIGS. 3, 8, and 13.

TABLE 9

| SEQ ID NO: | Primer name | Sequence listing (5'-3') |
|---|---|---|
| 4 | MITF_F | CCAGCCTGGCGATCATGTCAT |
| 5 | MITF_R | GGTCTGGACAGGAGTTGCTG |

TABLE 9-continued

| SEQ ID NO: | Primer name | Sequence listing (5'-3') |
|---|---|---|
| 6 | tyrosinase_F | GGCCAGCTTTCAGGCAGAGG |
| 7 | tyrosinase_R | TGGTGCTTCATGGGCAAAAT |
| 8 | TRP1_F | TCTGTGAAGGTGTGCAGGAG |
| 9 | TRP1_R | CCGAAACAGAGTGGAAGGTT |

As it may be confirmed in FIGS. 3, 8, and 13, the mRNA expression of MITF, tyrosinase, and TRP1, which are transcriptional factors involved in melanogenesis, were increased when the mouse melanin cell line B16F10 was treated with the peptide composed of the amino acid sequence of SEQ ID NO: 1, 2, or 3.

Example 4: Western Blotting of Melanogenesis-Related Proteins

Melanocytes (B16F10 cell line) were seeded on 6-well culture plates at the density of 5×10$^4$ cells/well and incubated in an incubator for 24 hours, and the cells were treated with the peptides of the present invention with different concentrations. After 72-hour incubation, the cells were lysed, and the cells were subjected to western blotting using antibodies (antacruz biotechnology, USA) each specific to MITF and tyrosinase, which are the factors involved in melanogenesis. The results are shown in FIGS. 4, 9, and 14.

Figure 4:
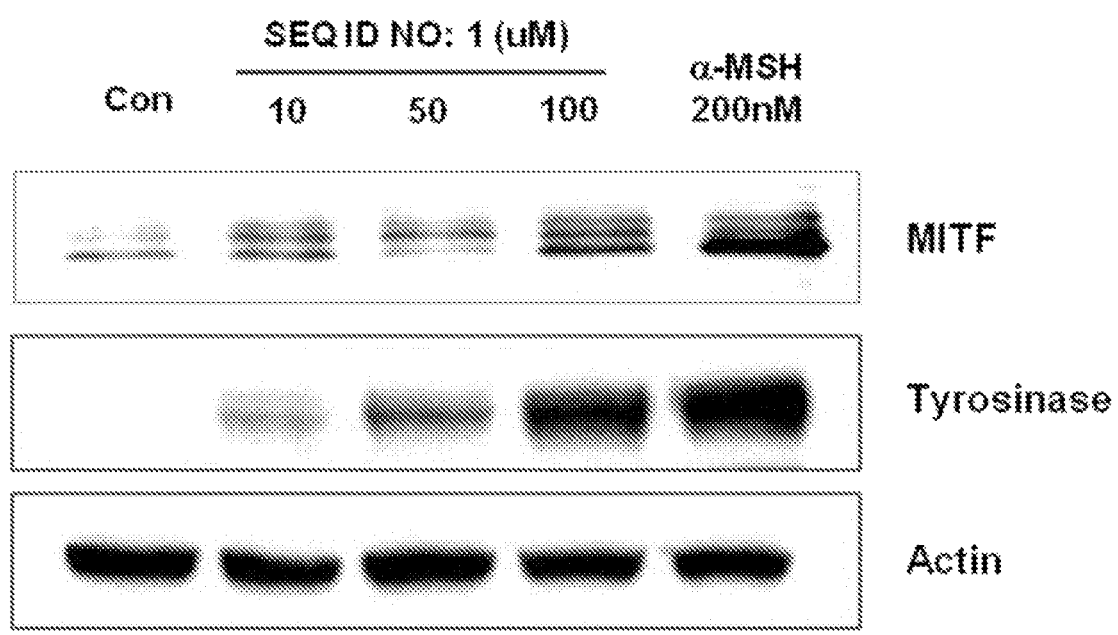
FIG. 4 shows a melanogenesis-related protein expression increasing effect of a peptide consisting of the amino acid sequence of SEQ ID NO: 1 according to an embodiment of the present invention.
Figure 9:
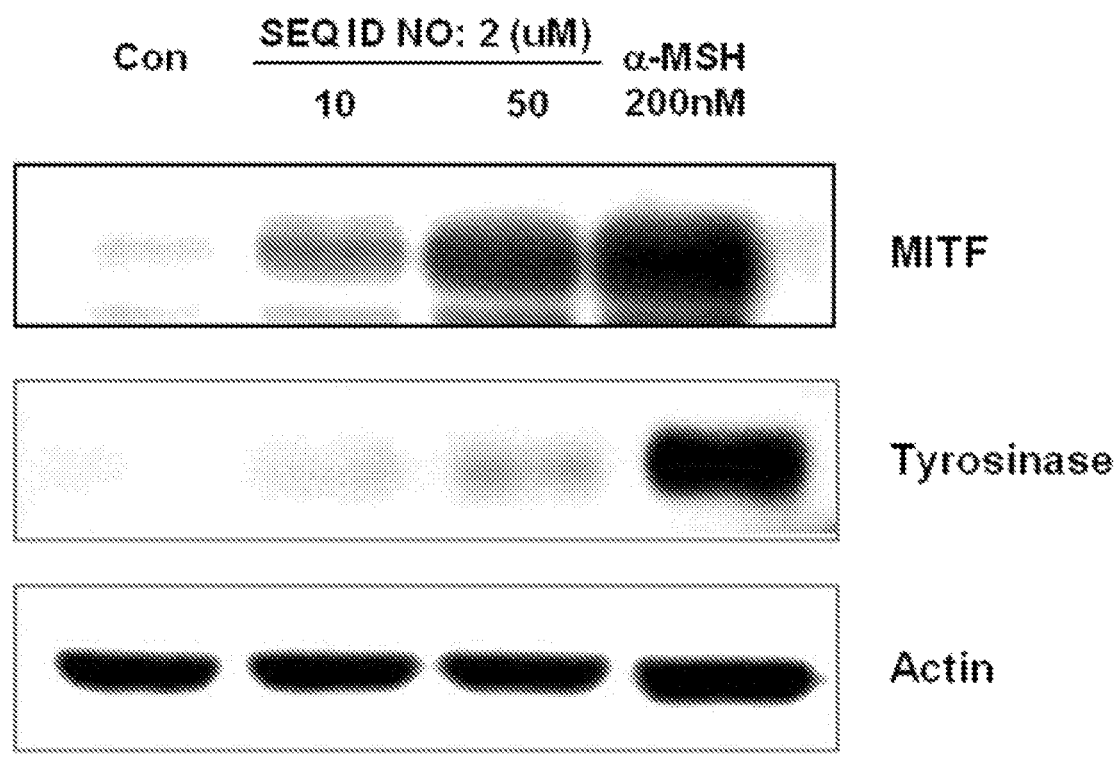
FIG. 9 shows a melanogenesis-related protein expression increasing effect of a peptide consisting of the amino acid sequence of SEQ ID NO: 2 according to an embodiment of the present invention.
Figure 14:
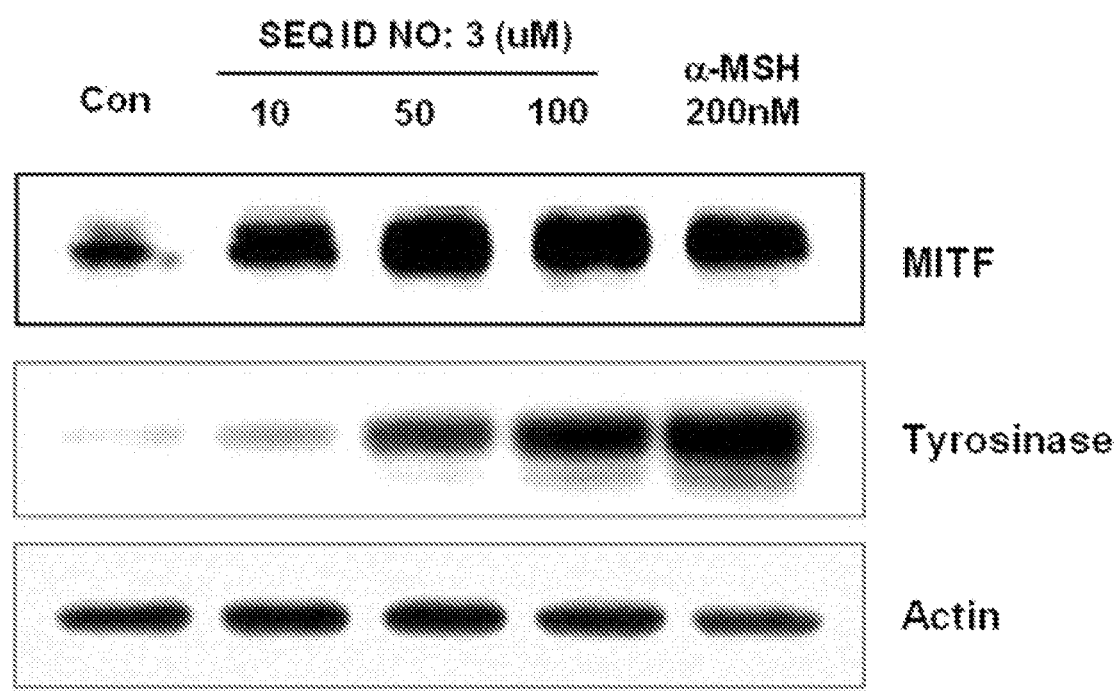
FIG. 14 shows a melanogenesis-related protein expression increasing effect of a peptide consisting of the amino acid sequence of SEQ ID NO: 3 according to an embodiment of the present invention.

As it may be confirmed in FIGS. 4, 9, and 14, the protein expression involved in the process of melanogenesis increased when the mouse melanin cell line B16F10 was treated with the peptide composed of the amino acid sequence of SEQ ID NO: 1, 2, or 3.

Example 5: Melanogenesis-Related Protein Activity Assay

Melanocytes (B16F10 cell line) were seeded on 6-well culture plates at the density of 5×10$^4$ cells/well and incubated in an incubator for 24 hours, and the cells were treated with the peptides of the present invention with different concentrations. After 48-hour incubation, the cells were lysed, and the cells were subjected to western blotting using specific antibodies (Cell Signaling Technology, USA) to investigate the phosphorylation level of CREB, which is a signaling substance involved in melanogenesis. The results are shown in FIGS. 5, 10, and 15.

Figure 5:
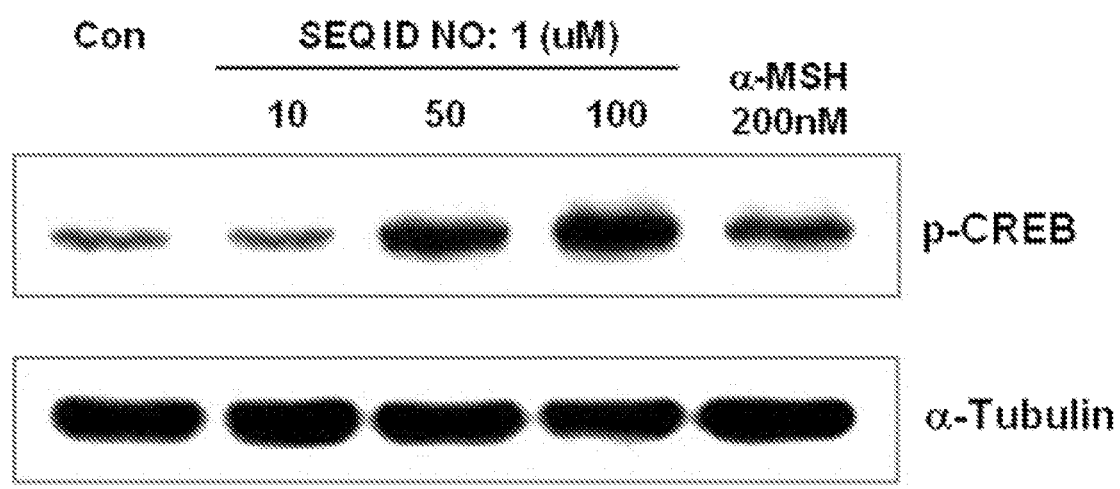
FIG. 5 shows an effect of increased phosphorylation of cAMP-responsive element binding protein (CREB) of a peptide consisting of the amino acid sequence of SEQ ID NO: 1 according to an embodiment of the present invention.
Figure 10:
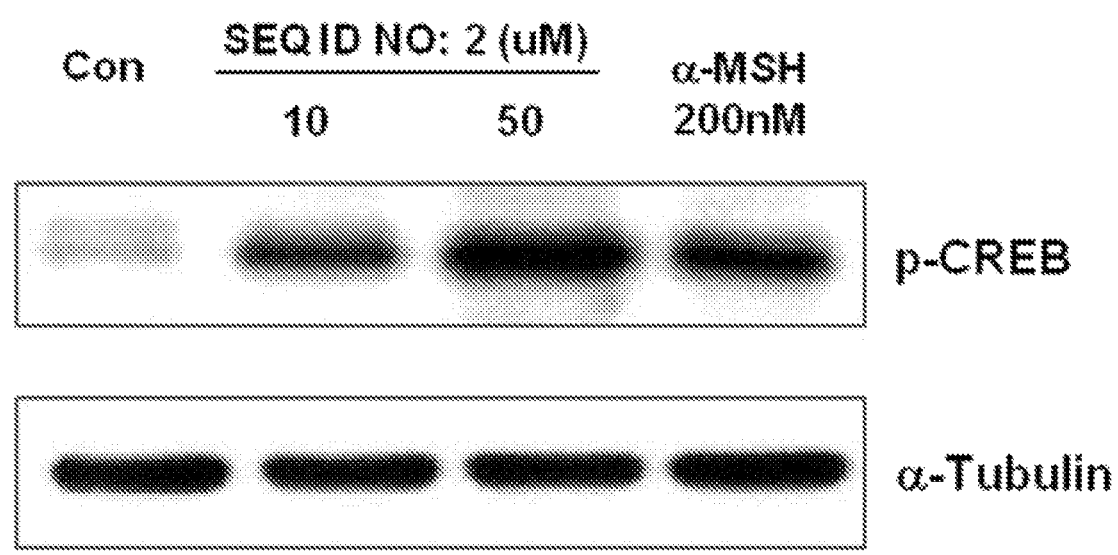
FIG. 10 shows an effect of increased phosphorylation of CREB of a peptide consisting of the amino acid sequence of SEQ ID NO: 2 according to an embodiment of the present invention.
Figure 15:
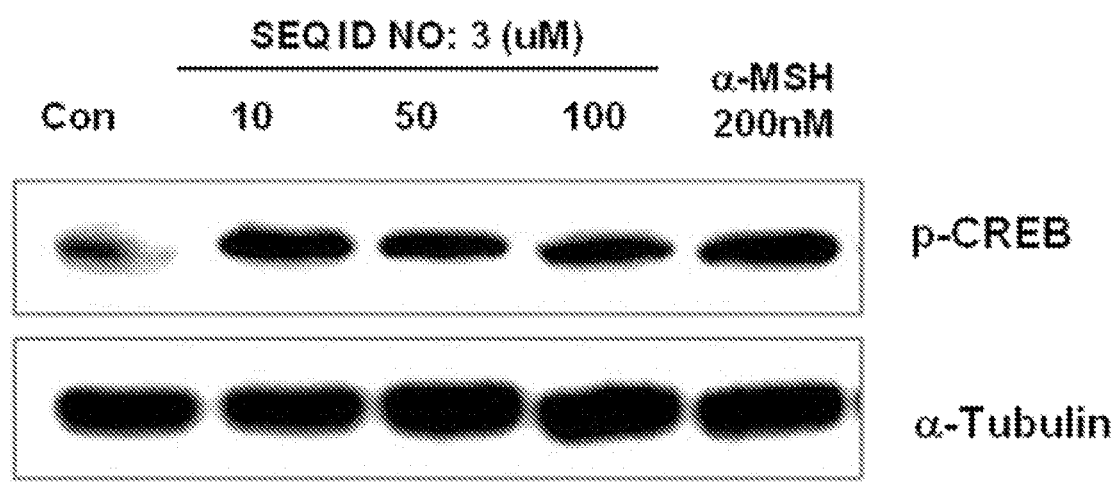
FIG. 15 shows an effect of increased phosphorylation of CREB of a peptide consisting of the amino acid sequence of SEQ ID NO: 3 according to an embodiment of the present invention.

As it may be confirmed in FIGS. 5, 10, and 15, the phosphorylation level of CREB, which is a factor involved in melanogenesis, was increased when the mouse melanin cell line B16F10 was treated with the peptide composed of the amino acid sequence of SEQ ID NO: 1, 2, or 3.

INDUSTRIAL APPLICABILITY

The present invention is related to a peptide showing melanogenesis promoting activity; a pharmaceutical composition for prevention and/or treatment of hypomelanosis including the peptide as an active ingredient; a cosmetic composition for prevention and/or alleviation of hypomelanosis including the peptide as an active ingredient; and the use of the peptide for prevention, alleviation, and/or treatment of hypomelanosis.

The invention claimed is:

1. A peptide consisting of the amino acid sequence SEQ ID NO: 2 or SEQ ID NO: 3, wherein (i) the C-terminal end of the peptide is modified by the presence of an amino group or an azide group, or (ii) the N-terminal end of the peptide comprises a protecting group.

2. The peptide of claim 1, wherein the C-terminal end of the peptide is modified by the presence of an amino group or an azide group.

3. The peptide of claim 1, wherein the N-terminal end of the peptide comprises a protecting group.

4. The peptide of claim 3, wherein the protecting group is selected from the group consisting of an acetyl group, a fluorenyl methoxy carbonyl group, a formyl group, a palmitoyl group, a myristyl group, a stearyl group, and polyethylene glycol (PEG).

5. A pharmaceutical composition for the treatment of hypomelanosis, comprising, as an active ingredient, at least one peptide selected from the group consisting of a peptide consisting of the amino acid sequence of SEQ ID NO: 2 and a peptide consisting of the amino acid sequence of SEQ ID NO: 3, optionally wherein (i) the C-terminal end of the peptide is modified by the presence of an amino group or an azide group, or (ii) the N-terminal end of the peptide comprises a protecting group.

6. The pharmaceutical composition of claim 5, wherein the hypomelanosis is vitiligo, albinism, nevus depigmentosus, pityriasis alba, pityriasis versicolor, post-inflammatory depigmentation, morphea, piebaldism, idiopathic guttate hypomelanosis, or leucoderma punctatum.

7. The pharmaceutical composition of claim 5, wherein the C-terminal end of the at least one peptide is modified by the presence of an amino group or an azide group.

8. The pharmaceutical composition of claim 5, wherein the N-terminal end of the at least one peptide comprises a protecting group.

9. The pharmaceutical composition of claim 8, wherein the protecting group is selected from the group consisting of an acetyl group, a fluorenyl methoxy carbonyl group, a formyl group, a palmitoyl group, a myristyl group, a stearyl group, and polyethylene glycol (PEG).

10. A cosmetic composition for the alleviation of hypomelanosis, comprising, as an active ingredient, at least one peptide selected from the group consisting of a peptide consisting of the amino acid sequence of SEQ ID NO: 2 and a peptide consisting of the amino acid sequence of SEQ ID NO: 3, optionally wherein (i) the C-terminal end of the peptide is modified by the presence of an amino group or an azide group, or (ii) the N-terminal end of the peptide comprises a protecting group.

11. The cosmetic composition of claim 10, wherein the hypomelanosis is vitiligo, albinism, nevus depigmentosus, pityriasis alba, pityriasis versicolor, post-inflammatory depigmentation, morphea, piebaldism, idiopathic guttate hypomelanosis, or leucoderma punctatum.

12. The cosmetic composition of claim 10, wherein the C-terminal end of the at least one peptide is modified by the presence of an amino group or an azide group.

13. The cosmetic composition of claim 10, wherein the N-terminal end of the at least one peptide comprises a protecting group.

14. The cosmetic composition of claim 13, wherein the protecting group is selected from the group consisting of an acetyl group, a fluorenyl methoxy carbonyl group, a formyl group, a palmitoyl group, a myristyl group, a stearyl group, and polyethylene glycol (PEG).

15. A method for the treatment or alleviation of hypomelanosis in a subject in need thereof, the method comprising administration of a peptide of claim 1 to the subject.

16. The method of claim 15, wherein the peptide is comprised within a pharmaceutical composition or a cosmetic composition.

17. The method of claim 15, wherein the C-terminal end of the at least one peptide is modified by the presence of an amino group or an azide group.

18. The method of claim 15, wherein the N-terminal end of the at least one peptide comprises a protecting group.

19. The method of claim 18, wherein the protecting group is selected from the group consisting of an acetyl group, a fluorenyl methoxy carbonyl group, a formyl group, a palmitoyl group, a myristyl group, a stearyl group, and polyethylene glycol (PEG).

20. The method composition of claim 15, wherein the hypomelanosis is vitiligo, albinism, nevus depigmentosus, pityriasis alba, pityriasis versicolor, post-inflammatory depigmentation, morphea, piebaldism, idiopathic guttate hypomelanosis, or leucoderma punctatum.

* * * * *

SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Phe Cys Leu Gly Pro Cys Pro Tyr Ile Trp Ser Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Lys Val Thr Ala Met Arg Cys Phe Leu Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Arg Val Thr Ala Met Arg Cys Phe Leu Leu
1               5                   10

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
ccagcctggc gatcatgtca t                                             21

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
ggtctggaca ggagttgctg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
ggccagcttt caggcagagg                                               20

<210> SEQ ID NO 7

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tggtgcttca tgggcaaaat                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
tctgtgaagg tgtgcaggag                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ccgaaacaga gtggaaggtt                                                   20
```